(12) United States Patent
Semnani et al.

(10) Patent No.: US 11,793,621 B2
(45) Date of Patent: Oct. 24, 2023

(54) DENTAL ANESTHETIC DELIVERY DEVICES AND ASSOCIATED METHODS

(71) Applicant: Hoodoo Voodoo, LLC., Salt Lake City, UT (US)

(72) Inventors: Rodmehr Tivon Bayegan Semnani, Salt Lake City, UT (US); Ria Sandhu, Sandy, UT (US); Elizabeth Stauder, Morgan, UT (US); LeAnn Lam, Murray, UT (US)

( * ) Notice: Subject to any disclaimer, the term of this patent is extended or adjusted under 35 U.S.C. 154(b) by 1063 days.

(21) Appl. No.: 16/584,639

(22) Filed: Sep. 26, 2019

(65) Prior Publication Data

US 2020/0268496 A1 Aug. 27, 2020

Related U.S. Application Data

(60) Provisional application No. 62/811,286, filed on Feb. 27, 2019.

(51) Int. Cl.
*A61C 19/08* (2006.01)
*A61M 5/30* (2006.01)
*A61M 5/20* (2006.01)

(52) U.S. Cl.
CPC ........... *A61C 19/08* (2013.01); *A61M 5/2046* (2013.01); *A61M 5/3007* (2013.01); *A61M 2202/048* (2013.01); *A61M 2210/0631* (2013.01)

(58) Field of Classification Search
CPC ... A61C 19/08; A61M 5/2046; A61M 5/3007; A61M 2202/048; A61M 2210/0631; A61M 5/30; A61M 2005/3139; A61M 5/3137
See application file for complete search history.

(56) References Cited

U.S. PATENT DOCUMENTS

| | | | | |
|---|---|---|---|---|
| 2,653,602 A * | 9/1953 | Smoot | ..................... | A61M 5/30 91/52 |
| 3,561,443 A * | 2/1971 | Banker | .................... | A61M 5/30 604/71 |
| 3,945,379 A * | 3/1976 | Pritz | ....................... | A61M 5/30 604/70 |
| 4,159,713 A * | 7/1979 | Prais | ................ | A61B 5/150244 604/222 |
| 4,766,843 A * | 8/1988 | Murakami | ......... | G03G 15/2053 428/35.8 |
| 6,200,289 B1 | 3/2001 | Hochman et al. | | |
| 6,224,378 B1 | 5/2001 | Valdes et al. | | |
| 6,652,482 B2 | 11/2003 | Hochman | | |
| 6,783,509 B1 * | 8/2004 | Landau | .................... | A61M 5/30 604/143 |
| 2016/0235917 A1 | 8/2016 | Bingham | | |

OTHER PUBLICATIONS

J-Tip Product Overview. National Medical Products. 2017, 3 pgs.

* cited by examiner

*Primary Examiner* — Theodore J Stigell (57) ABSTRACT

This disclosure relates to dental anesthetic delivery devices and associated methods for using the same. In certain embodiments, an anesthetic delivery device may comprise a pressure-driven needleless injector configured to deliver anesthetic deeply into the gingiva, allowing for a deep numbing and anesthetic effect and reducing pain from subsequent anesthetic injections and/or dental procedures. In some embodiments, the anesthetic delivery device may be T-shaped allowing for a shorter longitude axis length of the syringe body, improved clinician view of the oral cavity during use, single hand and/or ambidextrous use, and/or improved control during positioning.

20 Claims, 5 Drawing Sheets

DENTAL ANESTHETIC DELIVERY DEVICES AND ASSOCIATED METHODS

RELATED APPLICATION

This application claims the benefit of priority under 35 U.S.C. § 119(e) to U.S. Provisional Patent Application No. 62/811,286, filed Feb. 27, 2019, and entitled "Dental Anesthetic Delivery Devices and Associated Methods," which is hereby incorporated by reference in its entirety.

COPYRIGHT AUTHORIZATION

Portions of the disclosure of this patent document may contain material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

TECHNICAL FIELD

The present disclosure relates generally to the delivery of dental anesthesia. More specifically, but not exclusively, the present disclosure relates to devices for the delivery of dental anesthesia and associated methods.

SUMMARY

Many individuals experience anxiety when faced with the prospect of dental procedures. In some cases, this anxiety arises from fear of dental injections associated with dental anesthesia and/or associated discomfort or pain. Conventional methods for delivering dental anesthesia include an initial application of topical anesthetic (e.g., a topical gel anesthetic) to the gums followed by an injection of anesthetic using a dental syringe to obtain a deeper numbing and anesthetic effect. Topical anesthetic, however, may not fully numb an area, and patients may still experience pain during a subsequent anesthetic injection procedure.

Various embodiments disclosed herein provide for improved dental anesthetic delivery devices and associated methods for using the same. Certain embodiments of the disclosed devices and associated methods may reduce the pain associated with the delivery of dental anesthesia and, by extension, reduce patient anxiety relating to dental procedures. In certain embodiments, an anesthetic delivery device may comprise a pressure-driven needleless injector configured to deliver anesthetic (e.g., a topical anesthetic) deeply into the gingiva, allowing for a deep numbing and anesthetic effect and reducing pain from subsequent anesthetic injections and/or dental procedures.

Various embodiments of the disclosed anesthetic delivery device may comprise a dental needleless syringe that includes a syringe body and a handle portion. The handle portion may comprise one or more arms perpendicular to the longitudinal axis of the syringe body. In some embodiments, the dental needleless syringe device may be T-shaped, although other possible configurations are also contemplated. In certain embodiments, a gas canister may be disposed within at least one of the arms of the handle portion. In some embodiments, the gas canister may comprise a $CO_2$ gas canister. In various embodiments, the gas canister may be removable from the handle portion of the device.

A trigger mechanism may be disposed at a first end of the syringe body that, when pressed by a user, may break a pin and/or other suitable mechanism on the gas canister releasing gas into a gas chamber disposed within the syringe body. High pressure released from the gas canister into the chamber may drive a plunger and/or a piston within the syringe body downwards towards a second end of the syringe body. This action may force anesthetic (e.g., liquid topical anesthetic) disposed within an anesthetic chamber on an opposite side of the plunger and/or piston from the gas chamber within the syringe body through an orifice disposed on the second end of the syringe body at relatively high speeds. The anesthetic exiting the orifice may relatively painlessly puncture a patient's gingiva and deliver a deep numbing and/or anesthetic effect.

In various embodiments, the anesthetic delivery device may be shaped in a manner familiar to dental practitioners. In some embodiments, the T-shape of the disclosed anesthetic delivery device may allow for a shorter longitude axis length of the syringe body, improved clinician view of the oral cavity during use, single hand and/or ambidextrous use, and/or improved control during positioning and use than other needleless anesthetic delivery devices. In certain embodiments, the anesthetic delivery device may be loaded with anesthetic using standard anesthetic cartridges and/or syringes, thereby reducing costs associated with the use of the device.

Further embodiments disclosed herein provide for a method of delivering dental anesthetic using an anesthetic dental delivery device consistent with the various disclosed embodiments and/or loading such a device with anesthetic prior to use.

Consistent with embodiments disclosed herein, a dental anesthetic delivery device may comprise a syringe body that defines at least in part, a gas chamber and an anesthetic chamber. An orifice may be coupled to the syringe body that comprises a channel coupling an anesthetic delivery opening with the anesthetic chamber. In some embodiments, a cross-sectional profile of the channel of the orifice may taper between the anesthetic chamber and the anesthetic delivery opening.

A handle portion may be coupled to the syringe body that comprises at least one arm disposed at an angle relative to the syringe body. For example, in some embodiments, the at least one arm may be disposed perpendicular to the syringe body. In further embodiments, a plurality of arms may be used. In various embodiments, the syringe body, the handle portion, and/or the orifice may be integrally formed. The syringe body, the handle portion, and/or the orifice may be formed of a polycarbonate material, although other suitable materials and/or combinations thereof may also be used.

In certain embodiments, the syringe body and the orifice may be separately formed. For example, the orifice may be configured to couple with the syringe body using a mechanical structure such as, for example and without limitation, at least one of a threaded structure and/or a compression fit structure. In further embodiments, the orifice may be configured to couple with the syringe body using an adhesive.

The at least one arm may be configured to receive a gas cannister. In some embodiments, the gas cannister may be permanently received by the at least one arm using, for example, an adhesive and/or the like. In further embodiments, the gas cannister may be removably received by the at least one arm. For example, the handle portion may comprise at least one threaded structure, compression fit structure, and/or any other suitable mechanism configured to secure the gas canister within the at least one arm.

The dental anesthetic delivery device may further comprise a trigger mechanism disposed, at least in part, within the syringe body configured to actuate the gas cannister to release gas into the gas chamber. In some embodiments, the trigger mechanism may comprise a shaft configured to actuate a pin of the gas canister to release gas into the gas chamber. In further embodiments, the trigger mechanism may comprise a ring seal disposed around at least a portion of the shaft within the syringe body that may be configured to prevent the trigger mechanism from being ejected from the syringe body when the pressurized gas canister is actuated. The trigger mechanism may be formed of a polycarbonate material, although other suitable materials and/or combinations thereof may also be used.

In various embodiments, the dental anesthetic delivery device may also comprise a piston disposed within the syringe body separating the gas chamber from the anesthetic chamber. The piston may be configured to propel anesthetic disposed within the anesthetic chamber through the anesthetic delivery opening when the gas cannister is actuated. In some embodiments, the piston may comprise at least one rib disposed at least partially around a circumference of the piston. The piston may be formed of a Cis-1, 4-polyisoprene material, although other suitable materials and/or combinations thereof may also be used.

BRIEF DESCRIPTION OF THE DRAWINGS

The inventive body of work will be readily understood by referring to the following detailed description in conjunction with the accompanying drawings, in which.

DETAILED DESCRIPTION

A detailed description of the systems and methods consistent with embodiments of the present disclosure is provided below. While several embodiments are described, it should be understood that the disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

The embodiments of the disclosure may be understood by reference to the drawings, where in some instances, like parts may be designated by like numerals. The components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of any method disclosed herein do not necessarily need to be executed in any specific order, or even sequentially, nor need the steps be executed only once, unless otherwise specified.

Embodiments disclosed herein provide for dental anesthetic delivery devices and associated methods for using the same. An anesthetic delivery device consistent with embodiments disclosed herein may comprise an air and/or gas pressure-driven needleless injector configured to deliver anesthetic at a desired location deeply into a patient's gingiva. Various embodiments of the disclosed devices and/or associated methods may allow for an improved numbing and anesthetic effect when compared to conventional topical anesthetic applications and/or may reduce patient pain from subsequent anesthetic injections and/or dental procedures. Although various embodiments disclosed herein are described in connection with the use and/or delivery of dental anesthetic, it will be appreciated that embodiments of the disclosed devices and/or associated methods may further be used to deliver an analgesic and/or other types of medication in other suitable applications.

Figure 1:
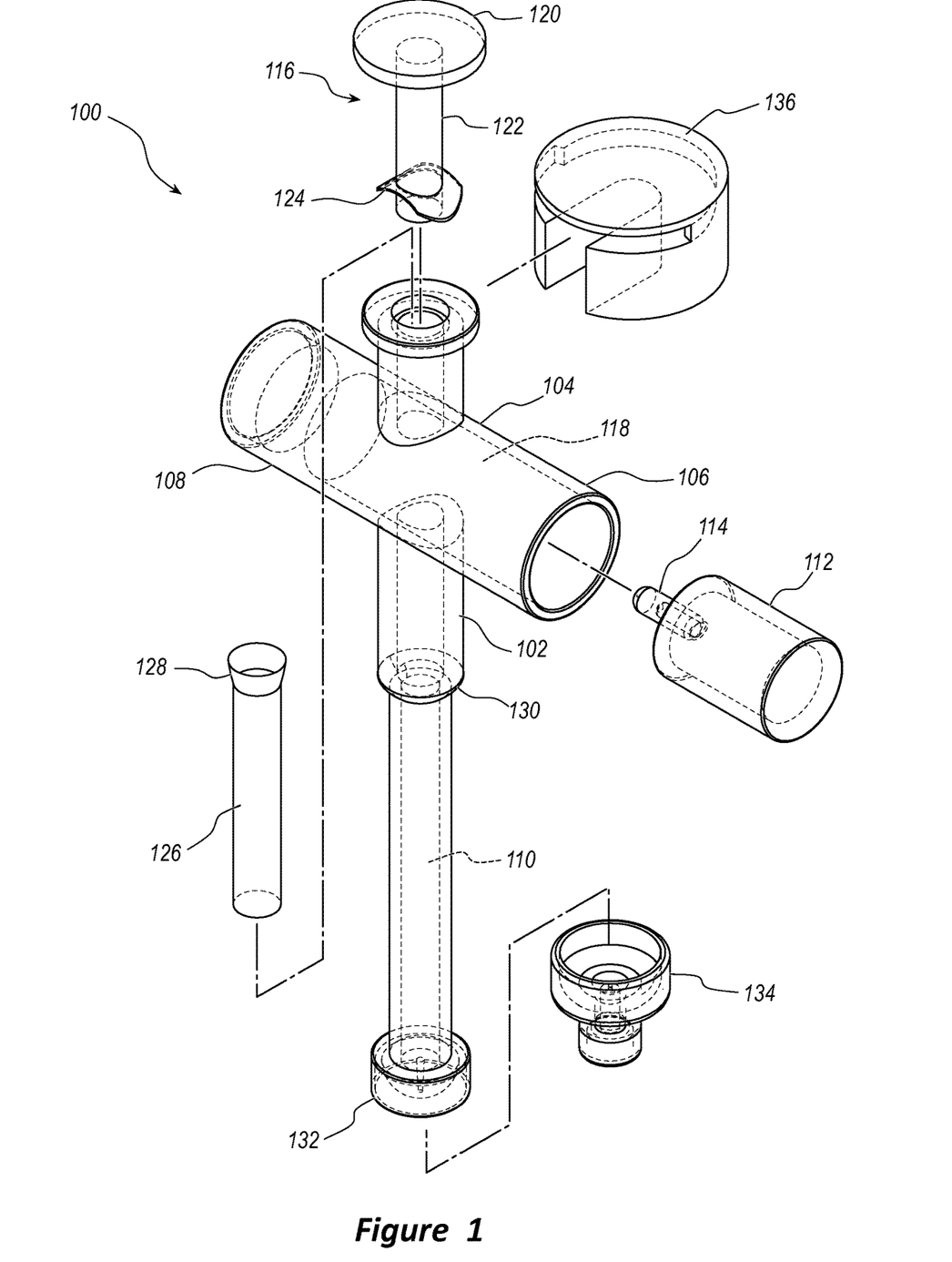
FIG. 1 illustrates an exploded view of a dental anesthetic delivery device and associated components consistent with certain embodiments of the present disclosure.
Figure 2:
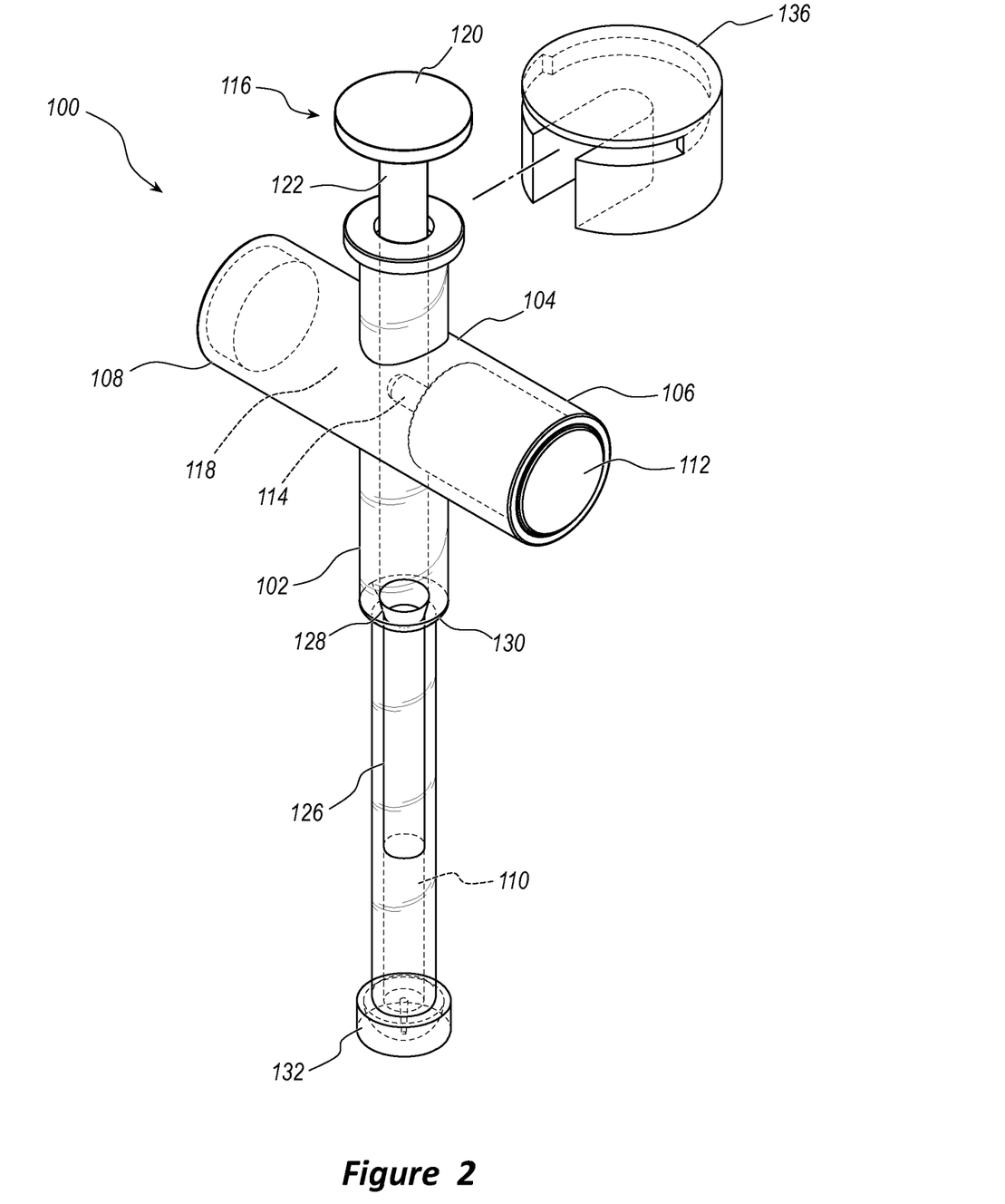
FIG. 2 illustrates a partially transparent view of an assembled dental anesthetic delivery device consistent with certain embodiments of the present disclosure.

FIG. 1 illustrates an exploded view of a dental anesthetic delivery device 100 and associated components consistent with certain embodiments of the present disclosure. FIG. 2 illustrates a partially transparent view of the assembled dental anesthetic delivery device 100 consistent with certain embodiments of the present disclosure. As illustrated in the figures, the dental anesthetic delivery device 100 may comprise a syringe body 102 and a handle portion 104. The handle portion 104 may comprise one or more arms 106, 108 perpendicular to the longitudinal axis of the syringe body 102. In some embodiments, the configuration of the handle portion 104 and the syringe body 102 may result in a T-shaped anesthetic delivery device 100.

It will be appreciated that in further embodiments, the syringe body 102 may include a handle portion 104 comprising fewer and/or additional arms 106, 108 than that shown in the figures in a variety of suitable configurations including, for example, configurations where the arms 106, 108 may not necessarily be disposed perpendicular to the longitudinal axis of the syringe body 102. For example, in some embodiments, one or more of the arms 106, 108 may be disposed at a non-perpendicular angle relative to the longitude axis of the syringe body 102.

In some embodiments, the syringe body 102 and the handle portion 104 may be integrally formed. In further embodiments, the syringe body 102 and the handle portion 104 may be separately formed and coupled using any suitable method and/or using any suitable structure. The various components of the dental anesthetic delivery device 100 may be formed using a variety of suitable types of material and using a variety of suitable methods, for example and without limitation, injection molding, 3-dimensional printing, computer numeric control ("CNC") machining, and/or any other suitable manufacturing technique and/or combination of techniques.

In certain embodiments, the syringe body 102 and/or handle portion 104 may comprise a polycarbonate material. For example, in some embodiments, the syringe body 102 and/or handle portion 104 may comprise a polycarbonate material having an elastic modulus at our about 2.0-2.4 GPa (e.g., approximately 98,627-522,135 psi), a melting point at or about 147-155° C., a compressive strength at or about 83 MPa (e.g., approximately 12,000 psi), a tensile strength ("UTS") at our about 66 MPa, and/or relatively robust chemical and impact resistance. It will be appreciated that suitable other types of polycarbonate material, as well as other types of materials and/or combination of materials, may also be used to form various components of the disclosed anesthetic delivery device 100.

In some embodiments, at least a portion of the syringe body 102 and/or handle portion 104 may comprise a transparent, semi-transparent, and/or a translucent material. For example, a portion of the syringe body 102 associated with an anesthetic chamber 110 and/or a portion thereof may be semi-transparent allowing for a clinician to view liquid anesthetic disposed within the anesthetic chamber 110 of the device 100. In certain embodiments, measurement indicators may be provided on the dental anesthetic delivery device 100, allowing a user of the device 100 to visually identify a volume of anesthetic that has been loaded into the anesthetic chamber 110. For example, measurement indicators may be provided on a transparent, semi-transparent, and/or translucent portion of the syringe body 102 associated with the anesthetic chamber 110 allowing a user to visually identify an amount of liquid anesthetic disposed within the chamber 110.

A gas canister 112 may be received and/or otherwise disposed within at least one of the arms 106, 108 of the handle portion 104. In some embodiments, the gas canister 112 may comprise a $CO_2$ gas canister. For example, the gas canister 112 may be filled with liquid $CO_2$ that may undergo a phase change into gaseous $CO_2$ when the canister 112 is breached. Although various embodiments of the dental anesthetic delivery device 100 are described herein as using a gas canister 112 that contains $CO_2$ gas, it will be appreciated that other types of pressurized gas canisters may also be used.

In certain embodiments, the gas cannister 112 may be breached by breaking and/or otherwise actuating an associated release pin 114. For example, as discussed in more detail below, the release pin 114 may be actuated using a trigger 116. In some embodiments, the pin 114 may be hollow and/or partially hollow such that the pin 114 is be sufficiently rigid to maintain form, but weak enough to be broken by the trigger 116 with relatively low force (e.g., less than 50 N).

The gas canister 112 may be formed using a variety of suitable materials and/or combination of materials and be configured to withstand the pressures exerted by its contents and during the release of its contents after being breached. In some embodiments, the gas canister 112 may be formed of a polycarbonate material. For example, the gas cannister 112 may comprise a polycarbonate material having an elastic modulus at our about 2.0-2.4 GPa (e.g., approximately 98,627-522,135 psi), a melting point at or about 147-155° C., a compressive strength at or about 83 MPa (e.g., approximately 12,000 psi), a UTS at our about 66 MPa, and/or relatively robust chemical and impact resistance. In some embodiments, the gas canister may be configured to store its contents at pressures above or about 870 psi (e.g., approximately 59.2 atm).

The gas cannister 112 may be configured to be securely disposed within an arm 106 of the handle portion 104 of the dental anesthetic delivery device 100 such that, when the cannister 112 is breached, its contents will expand into a gas chamber 118 defined within the syringe body 102 without significant amounts of gas escaping from the gas chamber 118.

The gas canister 112 may be secured into the handle portion 104 of the device 100 in a variety of ways and/or using a variety of mechanisms and/or combinations of mechanisms. For example, in some embodiments, the gas cannister may be secured within the handle portion using a compression fit mechanism, an adhesive, and/or the like. In some embodiments, the gas canister 112 may be secured into at least one arm 108 of the handle portion 104. For example, as illustrated, the gas canister 112 may be secured into a first arm 106 of the handle portion 104 of the device 100 and/or be oriented perpendicularly and/or at an angle relative to the longitudinal axis of the syringe body 102.

In further embodiments, the gas canister 112 may be removable from the handle portion 104 of the device 100. For example, the gas cannister 112 may be configured to interface with the handle portion 104 using a threaded interface mechanism, a compression fit and/or snap lock mechanism, and/or another removable mechanical mechanism and/or structure. In some embodiments, mechanisms that facilitate the removal of a used gas cannister 112 from the device 110 may also allow for reloading of a new gas canister, which allow for multiple uses of the anesthetic delivery device 100 with a patient.

Although various embodiments disclosed herein may use an actuated gas cannister 112 to release higher pressure gas into the gas chamber 118 of the device 100, it will be appreciated that a variety of other mechanisms and/or methods for generating higher pressure gas into the gas chamber 118 may be used in connection with various disclosed embodiments, including mechanisms that do not necessarily use a gas cannister 112. For example, in some embodiments, a spring-loaded and/or other mechanism may be used that, when actuated, cause a relatively rapid increase in air pressure within the gas chamber 118 of the device (e.g., by relatively rapidly changing a volume of the gas chamber 118 of the device 100). In at least one example, such a mechanism may comprise a spring-loaded piston that, when actuated, causes a plunger to move at a relatively rapid speed in a manner that, at least for a period of time, relatively rapidly changes a volume of the gas chamber 118, thereby increasing pressure within the gas chamber 118.

A trigger mechanism 116 may be disposed within a first end of the syringe body 102 that, when pressed by a user, may break the pin 114 and/or other release mechanism associated with the gas canister 112. This action may cause the gas cannister 112 to breach and release gas into a gas chamber 118 defined within the syringe body 102. In some embodiments, the trigger 116 may include a top actuation portion 120 and a shaft portion 122. The shaft portion 122 may rest upon and/or proximate to the gas cannister pin 114 and/or other associated release mechanism until the clinician is ready to deliver the anesthetic by pressing the actuation portion 120 of the trigger mechanism 116.

In certain embodiments, as described in more detail below, the trigger mechanism 116 may include a ring seal 124 disposed around at least a portion of the shaft portion 122 within the syringe body 102. In some embodiments, the ring seal 124 may be integral to the trigger mechanism 116.

In further embodiments, the ring seal 124 may comprise a separate structure mechanically and/or chemically coupled to the shaft portion 122 of the trigger mechanism 116. In various embodiments, the ring seal 124 may comprise the same material as the shaft portion 122 of the trigger mechanism 116. In other embodiments, the ring seal 124 may comprise a different material (e.g., rubber and/or the like) than the shaft portion 122 of the trigger mechanism 116.

The ring seal 124 may be configured to mitigate the potential for substantial amounts of gas from escaping through the first end of the syringe body 102 around the shaft portion 122 of the trigger mechanism 116 when the gas cannister 112 is breached. In addition, the ring seal 124 may mitigate the potential for the trigger mechanism 116 from being expelled outwards and/or otherwise separating from the syringe body 102 when the gas cannister 112 is breached.

The trigger mechanism 116 may be formed using a variety of suitable materials and/or combination of materials. In some embodiments, the trigger mechanism 116 may be formed of a polycarbonate material. For example, the trigger mechanism 116 may comprise a polycarbonate material having an elastic modulus at our about 2.0-2.4 GPa (e.g., approximately 98,627-522,135 psi), a melting point at or about 147-155° C., a compressive strength at or about 83 MPa (e.g., approximately 12,000 psi), a UTS at our about 66 MPa. and/or relatively robust chemical and impact resistance High pressure released from the gas canister 112 into the gas chamber 118 may cause a plunger and/or a piston 126 disposed within the syringe body 102 to be forced downwards towards a second end of the syringe body 102. In some embodiments, an arm 108 of the handle portion 104 of the device 110 may comprise an interior portion defining a wall of the gas chamber 118 opposite the gas cannister 112 that may be configured to direct the released gas within the gas chamber 118 toward the plunger and/or piston 126. The plunger and/or piston 126 may be formed using a variety of suitable materials and/or combination of materials. In some embodiments, the plunger and/or piston 126 may comprise Cis-1, 4-polyisoprene (i.e., isoprene rubber). For example, the plunger and/or piston may comprise Cis-1, 4-polyisoprene having a tensile strength at our about 19-21.6 MPa (e.g., approximately 3130 psi), an elongation at break at or about 428%, a 300% modulus at or about 8.60-13.5 MPa (e.g., 1250-1960 psi), and/or good relative resilience.

In certain embodiments, the plunger and/or piston 126 may comprise one or more portions having smooth and/or relatively smooth exterior walls as may be seen, for example, in FIG. 1 and FIG. 2. In further embodiments, the plunger and/or piston 126 may comprise one or portions having exterior ribs around at least a portion of a circumference of the plunger and/or piston 126 configured to create a seal against interior walls defined by the syringe body 102 as may be seen, for example, in FIG. 5.

Referring back to FIG. 1 and FIG. 2, in various embodiments, the shape and/or structure of the plunger and/or piston 126 may be configured to interface with interior walls defined by the syringe body 102 such that the plunger and/or piston 126 may maintain separation between the gas chamber 118 and the anesthetic chamber 110 within the device 100 and/or mitigate the escape of gas from the gas chamber 118 when the gas cannister 112 is breached. For example, the plunger and/or piston 126 may maintain and/or substantially maintain separation between the gas chamber 118 and the anesthetic chamber 110 when anesthetic is loaded into the anesthetic chamber 110 and/or when gas is released into the gas chamber 118 following actuation of the gas cannister 112.

In certain embodiments, the plunger and/or piston 126 may include a flared portion 128 which may restrict, at least in part, movement of the plunger and/or piston 126 within the syringe body 102 of the device 100 when gas is released into the gas chamber 118 following breach of the gas ganister 112. For example, movement of the flared portion 128 of the plunger and/or piston 126 past a corresponding narrowed portion 130 of the chamber defined within the syringe body 102 may be restricted. This configuration may, among other things, prevent substantial amounts of gas from escaping from the gas chamber 118 past the plunger and/or piston 126 into the anesthetic chamber 110 and/or may prevent the plunger and/or piston from contacting an orifice 132 of the device 100 at high speeds when the gas canister 112 is breached. It will be appreciated, however, that other embodiments may or may not include such a flared portion 128.

Figure 5:
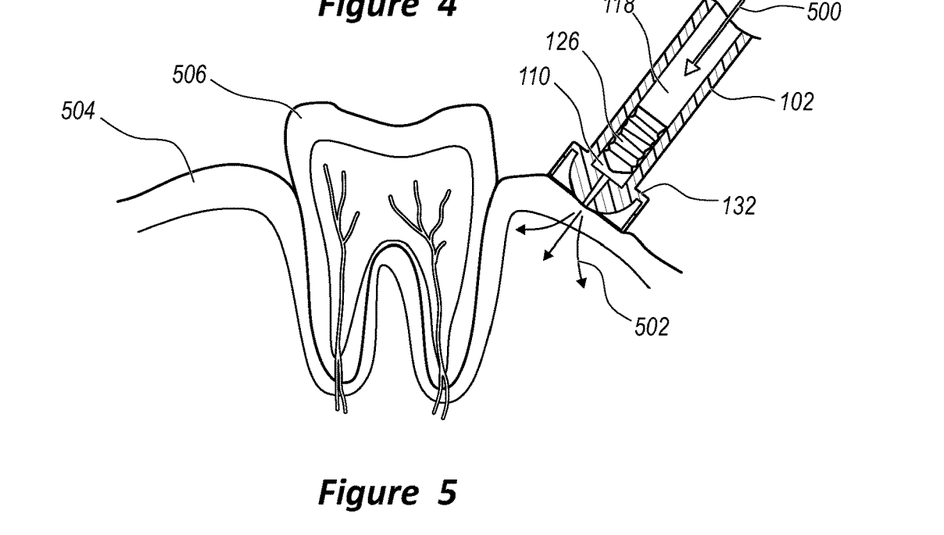
FIG. 5 illustrates a cross sectional view showing an example of the use of a dental anesthetic delivery device consistent with certain embodiments of the present disclosure.

As can be readily seen in connection with FIG. 5, which illustrates a cross sectional view showing an example of the use of a dental anesthetic delivery device 100 consistent with certain embodiments of the present disclosure, as the plunger and/or piston 128 are forced by the pressure of expanding gas 500 in the gas chamber towards the second end of the syringe body 102 (e.g., a distal end of the syringe body), anesthetic 502 disposed within an anesthetic chamber 110 on an opposite side of the plunger and/or piston 126 from the gas chamber 118 within the syringe body 102 may be propelled at high speeds through an orifice 132 disposed on the second end of the syringe body 102. The anesthetic 502 exiting the orifice 132 may relatively painlessly puncture a patient's gingiva 504 (e.g., a patient's gingiva 504 near a tooth 506 undergoing a dental procedure) and deliver a deep numbing and anesthetic effect to the area.

Figure 3:
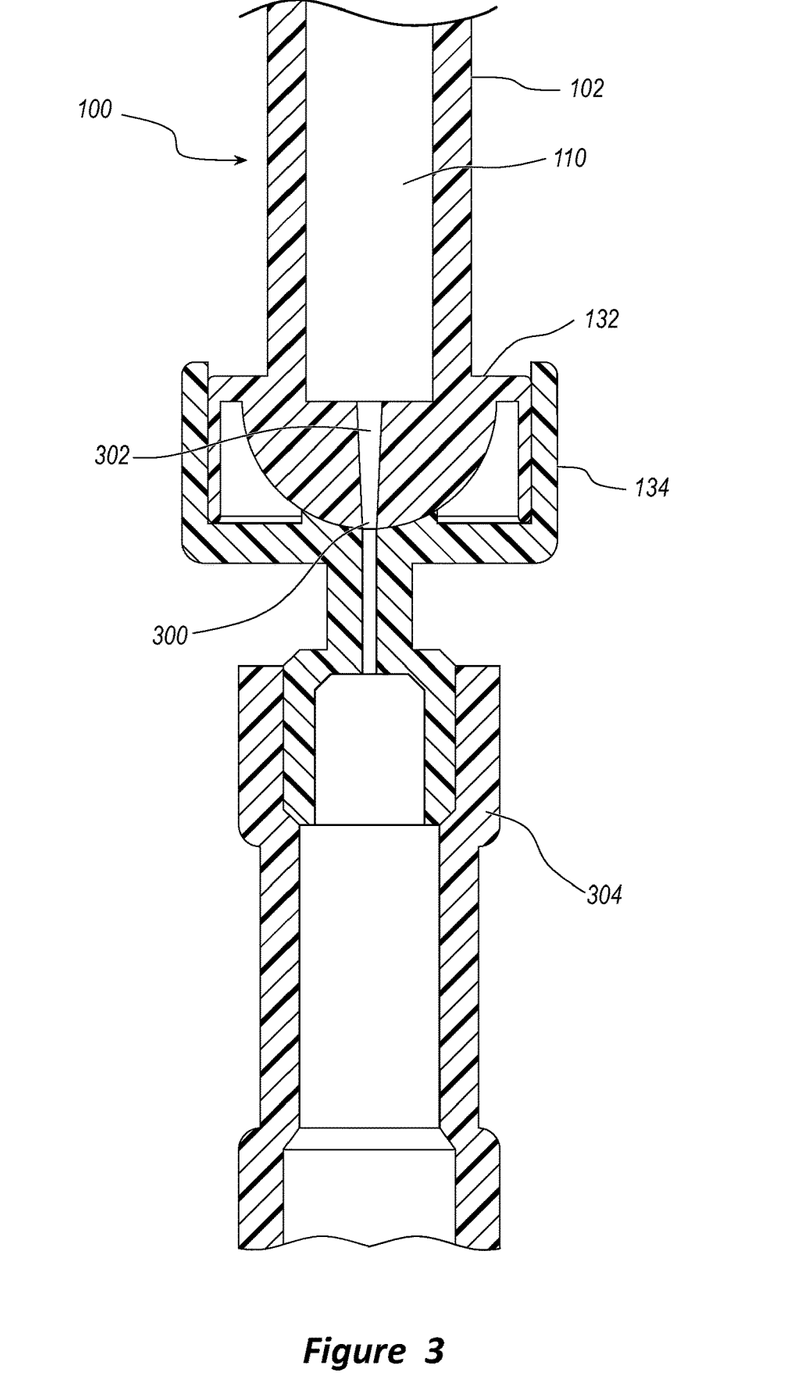
FIG. 3 illustrates a cross sectional view of a dental anesthetic delivery device orifice, a dental syringe adapter, and a loading syringe consistent with certain embodiments of the present disclosure.

Referring to FIG. 3, which illustrates a cross sectional view of a dental anesthetic delivery device orifice 132, a dental syringe adapter 134, and a loading dental syringe 300 consistent with certain embodiments of the present disclosure, in some embodiments, the orifice 132 may be integrally formed with the syringe body 102. In further embodiments, the syringe body 102 and the orifice 132 may be separately formed and coupled using any suitable method and/or via any suitable structure and/or combinations thereof (e.g., via a threaded interface, a compression fit, and/or any other suitable mechanical mechanism, via an adhesive and/or other chemical bonding agent, etc.). In some embodiments, the orifice 132 may be formed of a polycarbonate material. For example, the orifice 132 may comprise a polycarbonate material having an elastic modulus at our about 2.0-2.4 GPa (e.g., approximately 98,627-522,135 psi), a melting point at or about 147-155° C., a compressive strength at or about 83 MPa (e.g., approximately 12,000 psi), a UTS at our about 66 MPa, and/or good relative chemical and impact resistance. In certain embodiments, the orifice 132 may be removably coupled to the syringe body 102, allowing for different orifices to be used with the anesthetic delivery device 100 depending on a desired application.

In certain embodiments, the orifice 132 may comprise an opening 300. The opening 300 may, in some embodiments, have a diameter at or about 200 microns, although other suitable diameters are also contemplated. During actuation of the device 100, liquid anesthetic may be forced from the anesthetic chamber 110 through an orifice channel 302 to the opening 300 of the orifice 132 when the plunger and/or piston are forward towards the distal end of the device 100.

In certain embodiments, the orifice channel 302 between the opening 300 and the anesthetic chamber 110 may have a conical and/or otherwise narrowing cross-sectional profile. In some embodiments, the cross-sectional profile of the orifice channel 302 may be configured to allow the liquid anesthetic to exit the device 100 at relatively high speed and/or pressure and relatively painlessly puncture a patient's gingiva to deliver a deep, localized numbing and anesthetic effect in a desired area.

As described in more detail below, anesthetic may be both loaded into the anesthetic chamber 110 and delivered from the device 100 via the opening 300. In some embodiments, the opening 300 of the orifice 132 may be sized large enough to allow the anesthetic to be loaded into and to exit the device 100, but small enough to hold the anesthetic without leakage and/or without significant leakage until the device 100 is actuated via the trigger mechanism. In certain embodiments, the opening 300 of the orifice 302 may be sized to create sufficiently high pressures for the anesthetic to cross the gum barrier during operation of the device 100.

The cross-sectional profile of the orifice channel 302 between the opening 300 and the anesthetic chamber 110 may be configured to create sufficiently high pressure when the anesthetic exits the device 100 during operation. For example, in some embodiments, the channel 302 may have a conical cross-sectional profile that narrows and/or tapers as the channel 302 approaches the opening 300. The cross-sectional profile of the orifice channel 302 may further be configured to retain anesthetic within the anesthetic chamber 110 without leakage through the orifice 132 opening prior to actuation of the dental anesthetic delivery device 100. For example, a conical channel cross-sectional profile may allow anesthetic to exit the opening 300 at relatively high speeds/pressures when the gas cannister is breached during operation of the device 100, but may not allow a significant amount of anesthetic to leak through the opening 300 from the anesthetic chamber 110 prior to the gas cannister being breached.

In further embodiments, the specific configuration of the opening 300 and/or cross-sectional profile of the orifice channel 302 may depend in part on the properties of an anesthetic used in connection with the device 100. For example, the specific configuration of the opening 300 and/or cross-sectional profile of the orifice channel 302 may vary based on a flow rate, relative density, and/or relative viscosity of a liquid anesthetic used in connection with the dental anesthetic delivery device 100.

In certain embodiments, the dental anesthetic delivery device 100 may be loaded with anesthetic using a dental anesthetic syringe 304. For example, the anesthetic chamber 110 of the dental anesthetic delivery device 100 may be loaded with liquid anesthetic. A dental syringe adapter 134 may be used to provide a secure alignment and/or connection of the syringe body 102 of the anesthetic delivery device 100 and the dental anesthetic syringe 304 during loading operations. In some embodiments, the dental syringe adapter 134 may be configured to mechanically couple the anesthetic delivery device orifice 132 with a dental anesthetic syringe 304, allowing a user to load the anesthetic chamber 110 of the device 100 with anesthetic (e.g., liquid anesthetic) from the dental anesthetic syringe 304.

In some embodiments, the dental syringe adapter 134 may be configured to mechanically couple with the orifice 132 and/or syringe body 102 of the anesthetic delivery device 100 and with the dental anesthetic syringe 304 using one or more removable mechanical mechanisms and/or structures including, for example, one or more threaded mechanisms, Leur lock mechanisms, compression fit mechanisms, and/or any other suitable mechanism or combinations thereof. For example, in some embodiments, an outer circumference of the orifice 132 may be threaded and configured to couple to the dental syringe adapter 134 via a complementary threaded structure.

In certain embodiments, the dental syringe adapter 134 may comprise a female-to-female adapter, fitting both complementary male coupling structures on the dental anesthetic syringe 304 and the dental anesthetic delivery device 100. For example, in some embodiments, the dental syringe adapter 134 may comprise a threaded female-to-female adapter configured to interface with complementary male threaded structures on the dental anesthetic syringe 304 and the dental anesthetic delivery device 100. In further embodiments and as illustrated in connection with FIG. 3, the dental syringe adapter 132 may comprise a threaded female-to-male adapter configured to interface with a complementary male threaded structure on the dental anesthetic delivery device 100 and a complementary female threaded structure on the dental anesthetic syringe 304. In some embodiments, the structures may be coupled by neck portion of the dental syringe adapter 134. It will be appreciated that the dental syringe adapter 134, the dental anesthetic delivery device 100, and/or the dental anesthetic syringe 304 may comprise a variety of structures for coupling the adapter 134 with the dental anesthetic delivery device 100 and the dental anesthetic syringe 304, and that any suitable structure may be used in connection with the disclosed embodiments.

The dental syringe adapter 134 may comprise a variety of suitable materials and may be formed using a variety of suitable methods. In certain embodiments, the syringe adapter 134 may comprise acrylonitrile-butadiene-styrene ("ABS") having a tensile strength at or about 47 MPa, an elastic modulus at or about 2-2.6 GPa, and/or may be relatively resistant to heat and chemical exposure, although other suitable materials are also contemplated.

Referring back to FIG. 1 and FIG. 2, in various embodiments, a removable safety cap 136 may be used in connection with the anesthetic delivery device 100. In certain embodiments, when in place, the removable safety cap 132 may prevent the trigger mechanism 116 from being depressed by a user and/or by contact with an object during transport and/or storage, thereby mitigating the potential for accidental and/or otherwise inadvertent breach of the gas cannister 112. In certain embodiments, the safety cap 132 may comprise a structure that, when in place on the device 100, surrounds and/or at least partially surrounds at least a portion of the shaft portion 122 of the trigger mechanism 116 and/or physically maintains a minimum spacing between the top actuation portion of the trigger 120 and the syringe body 102, thereby physically preventing the trigger mechanism 116 from being depressed. In further embodiments and as illustrated in the figures, the safety cap 136 may further include a structure that covers the top actuation portion 120 of the trigger mechanism 116.

The safety cap 136 may comprise a variety of suitable materials and may be formed using a variety of suitable methods. In certain embodiments, the safety cap 136 may comprise ABS having a tensile strength at or about 47 MPa, an elastic modulus at or about 2-2.6 GPa, and/or may be relatively resistant to heat and chemical exposure, although other suitable materials are also contemplated.

Figure 4:
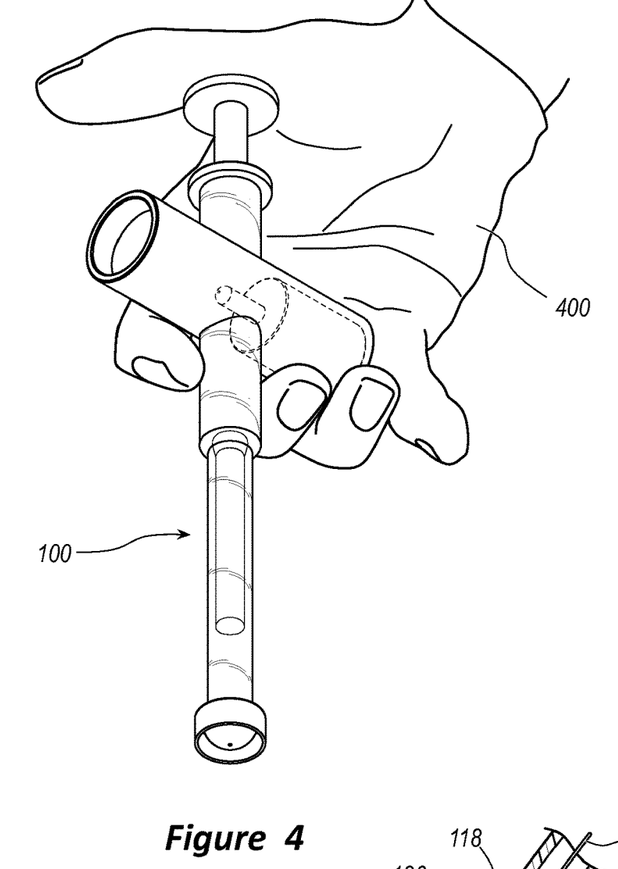
FIG. 4 illustrates an example of the use of a dental anesthetic delivery device by a clinician consistent with certain embodiments of the present disclosure.

FIG. 4 illustrates an example of the use of a dental anesthetic delivery device 100 by a clinician 400 consistent with certain embodiments of the present disclosure. As illustrated, the dental anesthetic delivery device 100 may be held by a clinician 400 and actuated by pressing the trigger mechanism with a thumb, palm, and/or other digit. In certain embodiments, the T-shape of the disclosed anesthetic delivery device 100 may allow for a shorter longitude axis length of the syringe body, improved clinician view of the oral cavity during use, single hand ambidextrous use, and/or improved control during positioning and use.

Referring to FIG. 5, during operation of the device, high pressure gas 500 released from the gas canister into the gas chamber 118 may drive the plunger and/or a piston downwards towards the orifice 132. This action may force anesthetic (e.g., liquid topical anesthetic) disposed within the anesthetic chamber 110 through the orifice 132 opening at relatively high speeds. The anesthetic 502 exiting the orifice 134 may painlessly puncture a patient's gingiva 504 and deliver a deep, localized numbing and anesthetic effect in a desired area.

In various embodiments, the anesthetic delivery device may be configured to deliver a variety of types of anesthetics and/or analgesics, as well as other medications. For example, in some embodiments, the anesthetic delivery device may be used to administer lidocaine, lidocaine with epinephrine HCl, and/or the like.

In certain embodiments, the anesthetic delivery device may exert an average pressure on the gums of below 5 psi. In some embodiments, the application surface area may be approximately between 17 mm$^2$ and 23 mm$^2$, although other areas are also contemplated. In various embodiments, the internal pressure within the anesthetic delivery device may less than approximately 900 psi when the device is first actuated. In some embodiments, the force required to press the trigger button and actuate the device may be less than 50 N and/or the force to load anesthetic in the device may be less than 35 N. In further embodiments, the flow rate through the device during loading operations may be at least approximately 0.5 ML/s, but less than approximately 3 mL/s. It will be appreciated that these pressures, application surfaces areas, forces, and flow rates are examples of various operational parameters, and that other operational parameters may be used in connection with various embodiments without departing from the scope of the inventive body of work.

Figure 6:
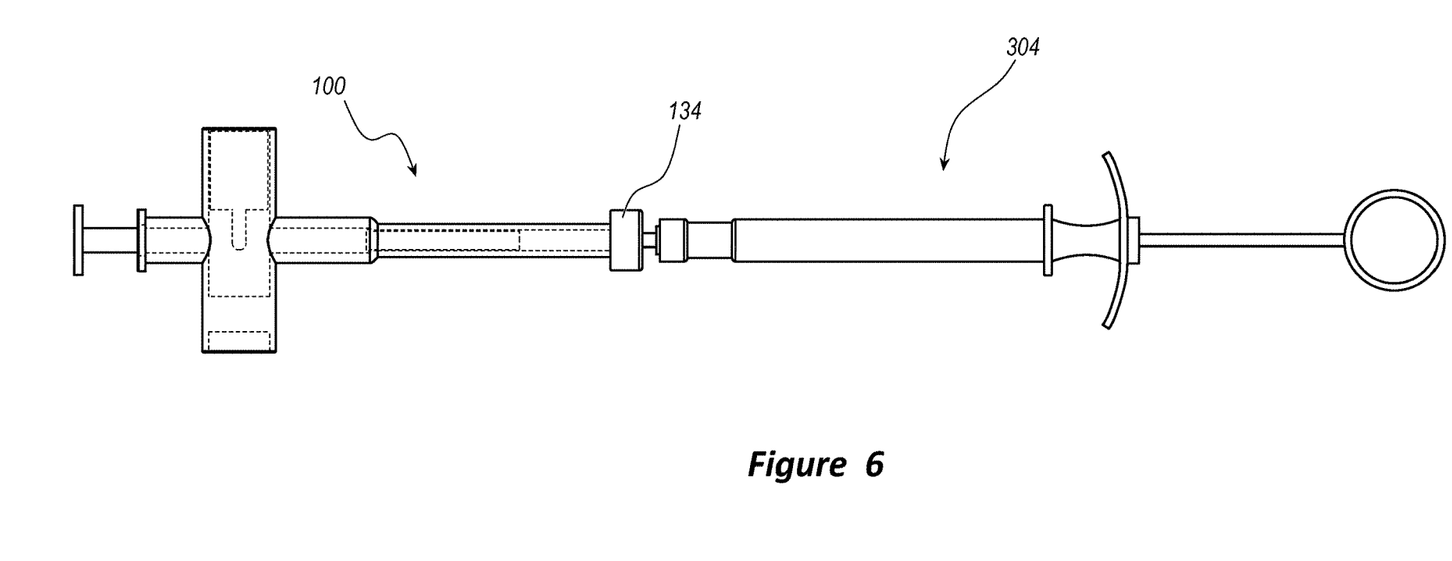
FIG. 6 illustrates loading of a dental anesthetic delivery device with a dental syringe and a dental syringe adapter consistent with certain embodiments of the present disclosure.

FIG. 6 illustrates loading of a dental anesthetic delivery device 100 using a dental syringe 304 and a dental syringe adapter 134 consistent with certain embodiments of the present disclosure. As illustrated, a dental syringe adapter 134 may be used to provide a secure alignment and/or connection of the anesthetic delivery device 100 and the dental anesthetic syringe 304 during loading operation. The dental syringe adapter 134 may be configured to mechanically couple with the anesthetic delivery device 100 and the dental anesthetic syringe 134, allowing a user to load the anesthetic chamber of the anesthetic delivery device 100 with liquid anesthetic from the dental anesthetic syringe 304. For example, in some embodiments, the dental syringe adapter 134 may be configured to provide a secure alignment of a needle and/or syringe associated with the dental syringe 304 with an orifice and/or associated opening of the dental anesthetic delivery device 100 during loading operations.

It will be appreciated that a number of variations can be made to the various embodiments and components presented in connection with the figures within the scope of the inventive body of work, and that the examples presented in the figures are provided for purposes of illustration and explanation, and not limitation. While various components are described as being formed using polycarbonate and/or ABS, it will be appreciated that a variety of other biocompatible materials and/or combinations of materials may be used in connection with the disclosed embodiments. For example, various components and/or aspects thereof may comprise glass (e.g., Type I glass, borosilicate glass, etc.), polypropylene, biocompatible metals, polyvinyl chloride, and/or any other suitable types of materials. In various embodiments, materials used in connection with embodiments of the disclosed anesthetic delivery device and/or components and/or aspects thereof may further be capable of being sterilized without significant deterioration or degradation.

Table 1, included below, details examples of possible dimensions of various components of a dental anesthetic delivery device consistent with some embodiments of the present disclosure. It will be appreciated that a number of variations can be made to the example dimensions and/or configurations presented in connection with Table 1 within the scope of the inventive body of work, and that the examples presented in Table 1 are provided for purposes of illustration and explanation, and not limitation.

TABLE 1

| Component | Component Element | Example Dimensions (mm) | Example Materials |
|---|---|---|---|
| Syringe Body | Total Dimensions | H117, W55, L18, Inner D15 | Polycarbonate |
| | Anesthetic Chamber | R2.5, H58, Th1.5 | |
| | Gas Chamber | R3, H15, Th 2.5 | |
| | Orifice | R0.1, H4, ⊖: 9° | |
| Syringe Adapter | Total Dimensions | H29, D15.8, TH2.15 | ABS |
| | Anesthetic Delivery Device Internal Face | R7.9, H17 | |
| | Neck | R1.25, H6 | |
| | Syringe Internal Face | R2.68, H6 | |
| | Syringe Threading | Female 0.75 × 6* | |
| Trigger Mechanism | Total Dimensions | H32, D17 | Polycarbonate |
| | Actuation Portion | R8.5, H2 | |
| | Shaft Portion | R2.85, H30 | |
| Gas Cannister | Total Dimensions | H30, D14.75 | Polycarbonate |
| | Body | R7.38, 1120, Th1.88 | |
| | Pin | R1.75, H10, Th.0.75 | |

TABLE 1-continued

| Component | Component Element | Example Dimensions (mm) | Example Materials |
|---|---|---|---|
| Safety Cap | Total Dimensions | H5, D20, Th2 | ABS |
| | Actuator Opening | R10, H2 | |
| | Shaft Opening | R3, L13 | |
| Piston and/or Plunger | Total Dimension | R2.78, H31 | Cis-1,4-polyisoprene |
| | Ribs | R0.5 × 3 | |

H: height; D: diameter; Th: wall thickness; R: radius; L: length; W: width; * metric female threading; ⊖: taper angle.

Although the foregoing has been described in some detail for purposes of clarity, it will be apparent that certain changes and modifications may be made without departing from the principles thereof. While various embodiments of the disclosed anesthetic delivery device are described in connection with delivering dental anesthesia and/or analgesia, it will be appreciated that in further embodiments, the disclosed devices and/or associated methods may be used in connection with a variety of other procedures in other clinical settings.

It should be noted that there are many alternative ways of implementing both the devices and methods described herein. Accordingly, the present embodiments are to be considered as illustrative and not restrictive, and the invention is not to be limited to the details given herein, but may be modified within the scope and equivalents of the appended claims.

What is claimed is:

1. A dental anesthetic delivery device comprising:
   a syringe body, the syringe body defining, at least in part, a gas chamber and an anesthetic chamber;
   an orifice coupled to the syringe body, the orifice comprising a channel coupling an anesthetic delivery opening with the anesthetic chamber,
   a handle portion coupled to the syringe body, the handle portion comprising at least one arm disposed at an angle relative to the syringe body, the at least one arm being configured to receive a gas cannister;
   a trigger mechanism, the trigger mechanism disposed, at least in part, within the syringe body, the trigger mechanism comprising a shaft configured to actuate the gas cannister to release gas into the gas chamber when the trigger mechanism is pressed in a direction parallel to the syringe body towards a distal end of the syringe body by a user, the shaft being configured to actuate the gas cannister by actuating a release pin of the gas canister to release gas into the gas chamber; and
   a piston disposed within the syringe body separating the gas chamber from the anesthetic chamber, the piston being configured to propel anesthetic disposed within the anesthetic chamber through the anesthetic delivery opening when the gas cannister is actuated.

2. The device of claim 1, wherein the at least one arm is disposed perpendicular to the syringe body.

3. The device of claim 1, wherein the at least one arm comprises a plurality of arms.

4. The device of claim 1, wherein the syringe body and the handle portion are integrally formed.

5. The device of claim 1, wherein the syringe body and the orifice are integrally formed.

6. The device of claim 1, wherein the syringe body and the orifice are separately formed, and the orifice is configured to couple with the syringe body using a mechanical structure comprising at least one of a threaded structure and a compression fit structure.

7. The device of claim 1, wherein the syringe body and the orifice are separately formed, and the orifice is configured to couple with the syringe body using an adhesive.

8. The device of claim 1, wherein the shaft is configured to actuate the release pin of the gas canister by breaking the release pin of the gas cannister.

9. The device of claim 1, wherein the trigger mechanism further comprises a ring seal disposed around at least a portion of the shaft within the syringe body.

10. The device of claim 9, wherein the ring seal is configured to prevent the trigger mechanism from being ejected from the syringe body when the gas canister is actuated.

11. The device of claim 1, wherein the at least one arm is configured to permanently receive the gas cannister.

12. The device of claim 11, wherein the gas cannister is configured to be coupled to the at least one arm using an adhesive.

13. The device of claim 1, wherein the at least one arm is configured to removably receive the gas cannister.

14. The device of claim 13, wherein the handle portion comprises at least one threaded structure configured to secure the gas canister within the at least one arm.

15. The device of claim 13, wherein the handle portion comprises at least one compression fit structure configured to secure the gas cannister within the at least one arm.

16. The device of claim 1, wherein the piston comprises at least one rib disposed at least partially around a circumference of the piston.

17. The device of claim 1, wherein a cross-sectional profile of the channel of the orifice tapers between the anesthetic chamber and the anesthetic delivery opening.

18. The device of claim 1, wherein the syringe body comprises a polycarbonate material.

19. The device of claim 1, wherein the trigger mechanism comprises a polycarbonate material.

20. The device of claim 1, wherein the piston comprises a Cis-1, 4-polyisoprene material.

* * * * *